United States Patent [19]

Rowles et al.

[11] 4,270,940
[45] Jun. 2, 1981

[54] RECOVERY OF $C_2$ HYDROCARBONS FROM DEMETHANIZER OVERHEAD

[75] Inventors: Howard C. Rowles, Center Valley; Tsun-chiu Tsao, Macungie, both of Pa.

[73] Assignee: Air Products and Chemicals, Inc., Allentown, Pa.

[21] Appl. No.: 92,894

[22] Filed: Nov. 9, 1979

[51] Int. Cl.³ .............................................. F25J 3/02
[52] U.S. Cl. ............................................ 62/28; 62/38; 62/31
[58] Field of Search ........................ 62/24–28, 62/38, 39, 31

[56] References Cited

U.S. PATENT DOCUMENTS

| | | | |
|---|---|---|---|
| 1,853,743 | 4/1932 | Pollitzer | 62/24 |
| 2,582,068 | 1/1952 | Roberts | 62/123 |
| 2,775,103 | 12/1956 | Koble et al. | 62/28 |
| 3,262,278 | 7/1966 | Thorsten et al. | 62/20 |
| 3,359,743 | 12/1967 | Di Napoli | 62/28 |
| 3,360,946 | 1/1968 | Di Napoli | 62/28 |
| 3,520,143 | 7/1970 | Becker | 62/28 |
| 3,675,435 | 7/1972 | Jackson et al. | 62/26 |
| 3,702,541 | 11/1972 | Randall et al. | 62/26 |
| 3,834,996 | 9/1974 | Aiso et al. | 62/28 |
| 4,002,042 | 1/1977 | Pryor et al. | 62/28 |

Primary Examiner—Norman Yudkoff
Attorney, Agent, or Firm—Richard A. Dannells, Jr.; James C. Simmons; E. Eugene Innis

[57] ABSTRACT

Enhanced recovery of ethane and ethylene from demethanizer overhead is obtained by subjecting the uncondensed vapor effluent from the main reflux condenser to further condensation and accompanying rectification in a dephlegmator and returning the liquid condensate from the dephlegmator to the demethanizer column. One or more of the refrigerants employed in the dephlegmator comprises vapors leaving the dephlegmator and cooled by pressure reduction.

10 Claims, 3 Drawing Figures

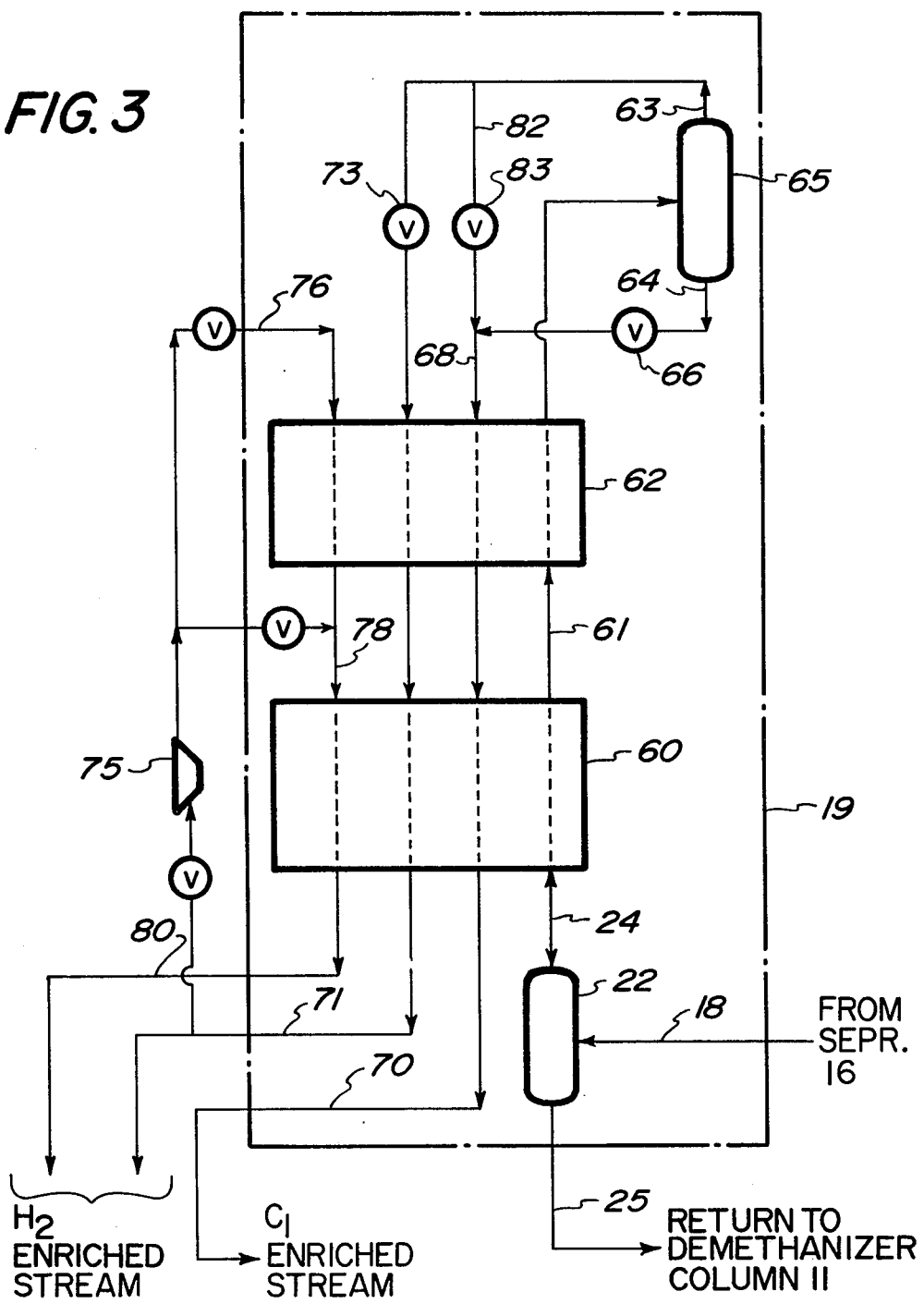

RECOVERY OF C₂ HYDROCARBONS FROM DEMETHANIZER OVERHEAD

BACKGROUND OF THE INVENTION

1. Field of the Invention

The present invention relates to low temperature separation of gaseous mixtures and is particularly concerned with enhancing recovery of ethylene and/or ethane from a mixture of hydrocarbons and low boiling gases containing the same.

2. Description of the Prior Art

Industrial plants for the recovery of $C_2$ hydrocarbons, particularly ethylene from admixture with methane and/or propane and propylene ($C_3$) and higher hydrocarbons are well-known. Such plants generally employ as part of the separation equipment a demethanizer column wherein the major portion of the methane content of the feed gas thereto is distilled as vapor overhead together with hydrogen, nitrogen, and any oxides of carbon that may be present. Practically all of the ethane and most of the ethylene are recovered as liquid in the bottoms fraction of the distillation column, together with $C_3$ and higher hydrocarbons. A small portion of the ethylene, however, present in the feed to the demethanizer distills over with the vapor fraction. In the conventional overhead reflux condenser associated with the demethanizer column, part of the ethylene in the overhead is condensed and returned to the column as reflux; a minor but valuable portion of the ethylene in the overhead, which may be as much as 20% or more, is not condensed and passes over from the reflux condenser with the methane vapor fraction. By provision of additional partial condensation approximately 10% of the ethylene remaining in the vapor leaving the main reflux condenser can be recovered.

The use of a typical demethanizer column in a system for recovery of $C_2$ hydrocarbons from a lean natural gas stream having a small $C_2+$ content (in the order of about 3.5 mol %) is illustrated, for example, in U.S. Pat. No. 3,360,946. The tabulated material balance of the patent discloses that only about 68% of the $C_2$ hydrocarbons are recovered. In a companion patent, U.S. Pat. No. 3,359,743, wherein the tail gas from the main reflux condenser of the demethanizer is further rectified, additional recovery of $C_2$ hydrocarbons is obtained; 8.7% of the $C_2$ hydrocarbons, however, are present in the final tail gas.

Demethanizer columns commonly employ low pressure ethane or ethylene as refrigerant to condense the overhead reflux. In some instances, Joule-Thompson (J-T) expansion refrigeration obtained from the overhead vapor product is utilized to provide auxiliary reflux, by partial condensation of the vapor leaving the main reflux condenser. In the case of a demethanizer column employed in an ethylene plant, such auxiliary partial condensation permits recovery of approximately 10% of the ethylene remaining in the vapor from the main condenser. Such processes are relatively inefficient in terms of the amount of ethylene recovered (10%) due to the extremely large amount of methane which must be condensed in order to recover the residual ethylene.

Various attempts to increase recovery of ethylene and/or ethane from demethanizer column overhead are disclosed, for example, in U.S. Pat. Nos. 3,262,278; 3,675,435 and 3,702,541.

Dephlegmators have been employed in the separation of binary gas mixtures, particularly where the components have widely separated boiling points, as exemplified in U.S. Pat. No. 2,582,068. Also in U.S. Pat. No. 4,002,042, directed to the recovery of the major portion of a $C_2+$ hydrocarbon fraction from a feed gas mixture comprising methane and hydrogen, the feed gas is introduced into a dephlegmator where it is cooled to form a condensate stream containing the major portion of the $C_2+$ hydrocarbons. The condensate stream, together with prior condensed material from the feed gas is passed to a demethanizer column. The uncondensed portion of the overhead vapor from the demethanizer column reflux condenser is utilized as one of the refrigerant streams in the dephlegmator.

Pending U.S. patent application Ser. No. 064,232, filed Aug. 6, 1979 discloses use of a dephlegmator for condensation and recovery of methane from ammonia plant purge gas or other industrial gas mixtures which contain hydrogen and one or more other low-boiling gases such as nitrogen and/or argon.

SUMMARY OF THE INVENTION

In accordance with the present invention, the auxiliary partial condenser heretofore employed in separation of $C_2$ hydrocarbons from the vapor fraction of the main reflux condenser of a demethanizer column is replaced by a dephlegmator. By such use of the dephlegmator, enhanced recovery of ethylene is obtained using the same J-T refrigeration. By further substituting an expansion engine for the overhead vapor stream J-T valve, thereby providing increased refrigeration for the dephlegmator, ethylene recovery can be increased to 90% or more. Such enhanced recovery of ethylene results from the rectification taking place in the dephlegmator. Since less of the methane and lighter components are condensed in the dephlegmator system than in the case of systems employing partial condensers, more of the available refrigeration is utilized to condense ethylene. The liquid stream produced in the dephlegmator is therefore more concentrated in ethylene.

BRIEF DESCRIPTION OF THE DRAWINGS

FIG. 3 is a schematic flow diagram of an alternative embodiment.

DETAILED DESCRIPTION

Figure 1:
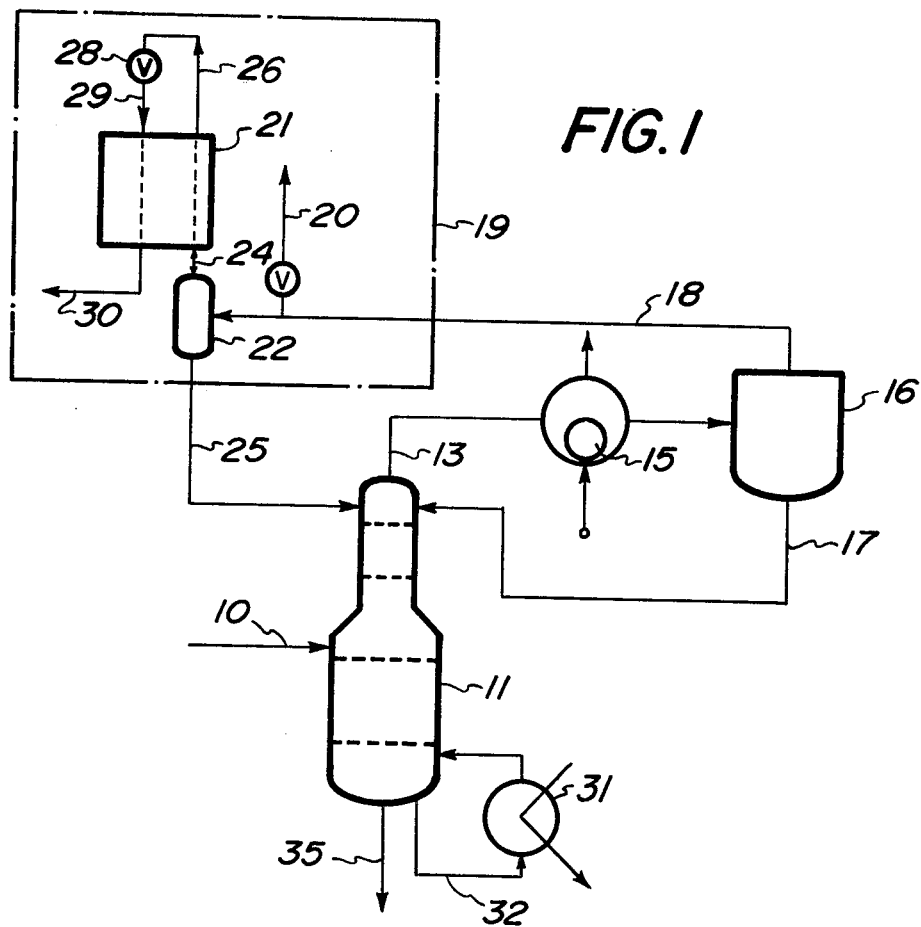
FIG. 1 of the accompanying drawings is a schematic flow diagram of a separation and recovery system in accordance with the present invention.

Referring to FIG. 1 of the drawings, the feed stream is introduced by line 10 into demethanizer column 11. A typical feed stream, for example, will contain:

|  | Mol % |
| --- | --- |
| Hydrogen | 12–15 |
| Carbon Monoxide | 0.1 |
| Methane | 30–40 |
| Ethane | 7–10 |
| Ethylene | 25–30 |
| $C_3+$ | 10–20 |
| Acetylene | 0–0.3 |

The feed stream, which will ordinarily contain mixed vapor and liquid components, is preferably introduced into the demethanizer column at a pressure in the range of about 30 to 40 atmospheres and at a temperature in the range of 195° to 230° K. The vapor overhead fraction, discharged from the demethanizer through line 13, is composed chiefly of hydrogen and methane but will usually contain about 2 to 5% of the ethane initially present in the demethanizer feed stream and about 15 to 20% of the original ethylene content thereof.

The vapor fraction in line 13 is cooled by indirect heat exchange with refrigerant, such as ethylene, in the main reflux condenser 15 to a temperature of about 170° to 195° K. and introduced into a phase separator 16. Separated liquid is returned to the demethanizer column as reflux via line 17.

The vapor fraction from the phase separator 16 is withdrawn by line 18 and passed into the cryogenic unit represented in the drawing by the dash-dot outline 19. If desired, a portion of the contents of line 18 may be withdrawn and sent to a hydrogen recovery system of known type, as indicated by branch line 20. In preferred operation less than 10%, generally not more than 3 to 5% of the total content of line 18 would be withdrawn for recovery of hydrogen. The remainder of the contents of line 18 is introduced into the lower zone of a dephlegmator 21 after being passed through phase separator 22. If required or desired, before entering separator 22, the products may be subjected to further cooling. In any event, the vapor mixture is desirably introduced into the lower zone of the dephlegmator at a temperature in the range of about 170° to 195° K.

The vapor flows in an upward direction in dephlegmator 21 through one or more indirect heat exchange passages (not shown), for further cooling. As the vapor is cooled, some of the mixture condenses on the walls of the passages, forming a reflux liquid that flows in a downward direction. Accordingly, interaction takes place between the stream of gas flowing upwards and the downwardly flowing stream of colder liquid. Rectification thus results whereby the gaseous mixture passing through the dephlegmator becomes enriched in $C_1$ and lighter components and the liquid leaving the dephlegmator is enriched in $C_2$ and any higher boiling components that may be present. The descending liquid stream is drained from the dephlegmator into separator 22 via the same line 24 through which the vapor overhead from separator 22 is passed upwardly into the dephlegmator, as denoted by the double arrow shown on that line. In separator 22, the liquid discharged from the dephlegmator is separated from the stream introduced into the separator by line 18.

The liquid stream discharged from separator 22 is returned to demethanizer 11 via line 25. The temperature of the liquid introduced into the demethanizer by line 25 will generally be somewhat lower than the vapor inlet temperature to the dephlegmator, as at a temperature in the range of about 168° to 194° K. This stream will contain in addition to methane and small amounts of residual hydrogen and ethane, up to about 10 to 20% of ethylene, which constitutes more than 2% of the ethylene contained in the initial mixed stream entering the demethanizer column via line 10.

The uncondensed vapor leaving the dephlegmator is reduced in pressure by J-T expansion valve 28 in line 26 with accompanying cooling and reintroduced into the dephlegmator by line 29 to serve as refrigerant for the vapor stream entering therein via line 24.

The tail gas leaving the dephlegmator via line 30 comprises chiefly methane and hydrogen and contains less than 1 mol % ethylene, which constitutes less than about 1% of the ethylene present in the initial feed gas to the demethanizer column.

Heat for the distillation in demethanizer column 11 is provided by reboiling in reboiler 31 and returning a portion of the liquid bottoms withdrawn from the column by line 32. The liquid fraction withdrawn from column 11 by line 35 consists almost entirely of $C_2+$ hydrocarbons.

Figure 2:
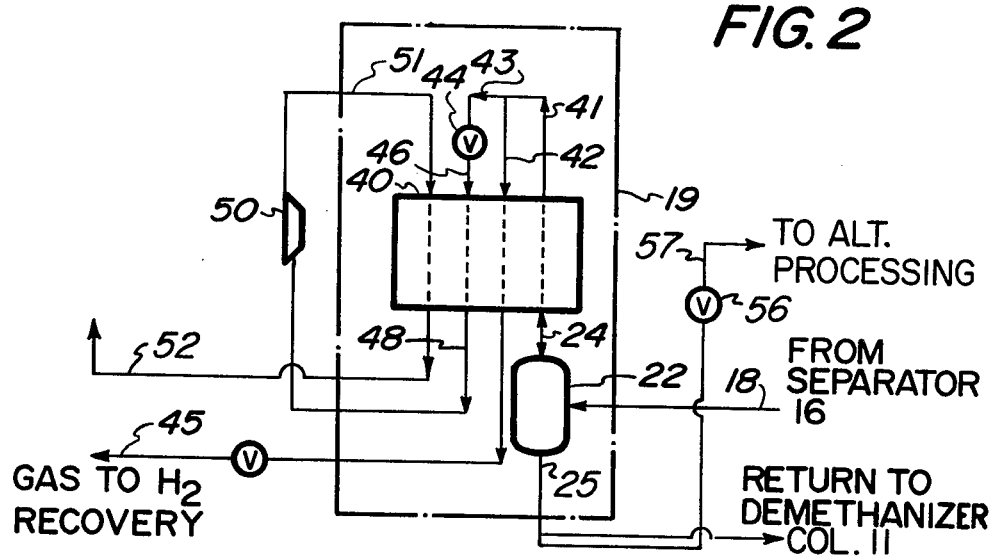
FIG. 2 is a schematic flow diagram of a preferred alternative embodiment of the cryogenic section employing an expansion engine to supply additional refrigeration for the dephlegmator.

FIG. 2 of the drawings illustrates a modified cryogenic unit for increased recovery of $C_2$ hydrocarbons from the demethanizer overhead vapors discharged from the main reflux condenser. It will be understood that the demethanizer column with its associated parts are the same as in FIG. 1 and are omitted from FIG. 2.

As shown in FIG. 2, the uncondensed vapors leaving the vapor-liquid reflux separator (16 in FIG. 1) by line 18 are admitted to the cryogenic unit 19. The vapors, as in the preceding embodiment, are introduced into phase separator 22 and the separated vapors flow upwardly through line 24 into the dephlegmator 40. The vapors are cooled by indirect heat exchange effecting condensation on the walls of the dephlegmator passages and the resulting liquid forms a reflux that flows downward in counter flow to the vapor. The uncondensed vapor is enriched in $C_1$ by rectification, while the reflux liquid is enriched in $C_2$ and heavier hydrocarbons to provide the liquid product discharged through line 24 to separator 22.

Cooling of the vapor in the dephlegmator 40 is effected by heat exchange in the provided passages (not shown) with a low pressure off gas stream, a high pressure off gas stream and the feed to a hydrogen recovery unit. Thus, as shown in FIG. 2, the overhead vapor leaving the dephlegmator 40 via line 41 is split into a stream (line 42) composed of that portion of the vapor to be sent to the hydrogen recovery plant, and a high pressure off gas stream (line 43). The stream in line 42 is passed through the dephlegmator 40 at substantially the same pressure at which the vapors were admitted through line 24 and at an attained temperature in the range of about 160° to 190° K. The stream in line 42 is warmed in the dephlegmator, raising its temperature by about 5° to 10° K., and is sent to the hydrogen recovery unit through line 45. In connection with a typical ethylene plant the product in line 45 is useful to maintain the desired hydrogen flow rate for the acetylene reactor.

The stream in line 43 may be flashed, as indicated at J-T valve 44, to an intermediate pressure prior to being passed through the dephlegmator via line 46, wherein it is warmed to a temperature in the range of 168° to 194° K. Leaving the dephlegmator by line 48, the stream is work expanded by turbine 50 with accompanying cooling and returned to the dephlegmator through line 51. Each of the streams in lines 42, 46, and 51 in passing through the several passages of the dephlegmator are warmed to a temperature in the range of 168° to 194° K. to provide the necessary refrigeration therein to effect the desired condensation and rectification of $C_2$ and heavier components from the vapor stream introduced by line 24. The off gas passing through dephlegmator 40 is discharged therefrom via line 52. As described in connection with FIG. 1, the collected liquid drained from the dephlegmator passes into separator 22 via line 24 and is withdrawn by line 25, through which it is returned as auxiliary reflux to the demethanizer column and ultimate recovery in the liquid products discharged by line 35 (FIG. 1).

The $C_2$ enriched liquid stream recovered in line 25 (FIG. 2) might also be processed by alternate means prior to recovery of the $C_2$ hydrocarbons contained therein. As an example, the liquid might be reduced in pressure by J-T valve 56 and passed via line 57 to become at least partially vaporized in dephlegmator 40 to provide increased refrigeration to the dephlegmator. The stream would then be recycled by suitable compression equipment and returned to the demethanizer column 11 for ultimate recovery of $C_2$ hydrocarbons.

FIG. 3 of the drawings illustrates a further embodiment in which $H_2$ recovery of a known type is combined with the $C_2$ hydrocarbon recovery system of the present invention to obtain high $H_2$ recovery. As in FIG. 2, demethanizer column 11 and its auxiliary equipment are omitted from FIG. 3 and the uncondensed vapors leaving separator 16 (FIG. 1) are introduced via line 18 into phase separator 22. The separated vapors flow upwardly via line 24 into dephlegmator 60. Uncondensed vapor leaving the top of the dephlegmator 60 via line 61 is subjected to partial condensation in heat exchanger 62 and the resulting $H_2$ enriched vapor (line 63) and $C_1$ enriched liquid (line 64) are separated by means of phase separator 65. The liquid in line 64 is reduced in pressure via J-T valve 66, and the vapor in line 63 and the liquid in line 68 are separately warmed in heat exchanger 62 prior to being utilized in dephlegmator 60 to provide the refrigeration necessary for condensation and rectification of the $C_2$ enriched liquid produced in the dephlegmator (line 25). The $C_1$ enriched stream is recovered from dephlegmator 60 via line 70 and the $H_2$ enriched vapor is recovered via line 71.

Alternatively, additional refrigeration may be provided by means to increase $C_2$ hydrocarbon recovery, such as J-T expansion by passing a portion of the $H_2$ enriched vapor in line 63 through J-T valve 73 or work expansion of the $H_2$ enriched vapor in line 71 through expander 75. The $H_2$ enriched stream is then returned either through heat exchanger 62 via line 76 and dephlegmator 60 via line 78 or only through dephlegmator 60 before the stream is discharged therefrom via line 80. A portion of the $H_2$ enriched stream in line 63 may also be combined with the $C_1$ enriched liquid in line 68 via line 82 and valve 83 to enhance refrigeration recovery.

EXAMPLE 1

The mixed vapor liquid stream charged to the demethanizer column of an ethylene plant is composed of:

|  | Mols |
|---|---|
| Hydrogen | 274.5 |
| Carbon Monoxide | 1.1 |
| Methane | 734.6 |
| Ethane | 158.1 |
| Ethylene | 567.7 |
| $C_3+$ | 285.0 |
| Total | 2021.0 |

This stream is introduced into the demethanizer column 11 via line 10 at a temperature of 208° K. and at a pressure of 498 psia (35 kg/cm²). There is obtained an overhead vapor fraction (line 13) comprising chiefly:

|  | Mol % |
|---|---|
| Hydrogen | 15.3 |
| Carbon Monoxide | 0.1 |
| Methane | 79.1 |
| Ethane | 0.3 |
| Ethylene | 5.2 |
| $C_3+$ | trace |
| Total | 100.0 |

The vapor fraction is cooled in reflux condenser 15° to 174° K. and introduced into phase separator 16 from which the condensed liquid fraction is returned to the demethanizer column as a reflux liquid fraction via line 17.

The overhead vapor fraction from the main reflux condenser is sent to the cryogenic unit 19 via line 18. It is comprised of

|  | Mol % |
|---|---|
| Hydrogen | 23.8 |
| Methane | 74.3 |
| Ethylene | 1.7 |
| Total | 99.8 | and 0.2 mol % of ethane, carbon monoxide and propane.

Employing the embodiment illustrated in FIG. 1, a portion constituting 4.4% thereof, is withdrawn from the stream in line 18 and sent to the hydrogen recovery unit via line 20. The remaining 95.6% is introduced into the dephlegmator 21 via separator 22 and line 24, at its attained pressure of 494 psia (34.7 kg/cm²) and temperature of 174° K.

In passing through the dephlegmator 21, the stream is cooled to 169° K. by heat exchange with the returning stream in line 29, effecting condensation and rectification of a portion thereof drained (via line 24) into the phase separator 22. The liquid returned as auxiliary reflux to the demethanizer column 11 (via line 25) is composed chiefly of 88.5% methane and 9% ethylene, at an attained temperature of 173° K.

The refrigeration for the dephlegmator 21 in the illustrated embodiment of FIG. 1 is provided by reducing the pressure of the uncondensed vapor in line 26 to 115 psia (8.1 kg/cm²) with consequent reduction in temperature to 144° K. The warmed off gas discharged through line 30 at 173° K. comprises 72% methane and 27% hydrogen. It contains less than 0.6 mol % of ethylene, which constitutes less than 1% of that initially present in the mixed feed charged to the demethanizer column.

The liquid product recovered from the demethanizer (line 35) at 502 psia (35.3 kg/cm²) and 288° K. comprises:

|  | Mol % |
|---|---|
| Ethane | 15.7 |
| Ethylene | 55.9 |
| $C_3+$ | 28.4 |
| Methane | trace |
| Total | 100.0 |

The ethylene recovery from the dephlegmator is over 70% of that present in the vapor stream entering the dephlegmator, in addition to which 90% or more of the ethane is recovered.

Even higher recovery is obtained when employing an expander instead of the J-T valve according to the embodiment of FIG. 2. An example of one such operation is set out in Example 2, below.

EXAMPLE 2

The mixed feed to the demethanizer column contains

|  | Mols |
| --- | --- |
| Hydrogen | 285.3 |
| Carbon Monoxide | 1.2 |
| Methane | 763.8 |
| Acetylene | 3.9 |
| Ethylene | 568.4 |
| Ethane | 154.3 |
| $C_3+$ | 285.0 |
| Total | 2061.9 |

The vapor overhead from the demethanizer column reflux condenser (line 18) contains

|  | Mols |
| --- | --- |
| Hydrogen | 291.5 |
| Carbon Monoxide | 1.3 |
| Methane | 1057.1 |
| Acetylene | 0.07 |
| Ethylene | 21.4 |
| Ethane | 0.7 |
| $C_3$ | 0.01 |
| Total | 1372.1 |

The vapor overhead stream from the main reflux condenser is introduced into the dephlegmator 40 (FIG. 2) at a temperature of 174° K. and at a pressure of 497 psia (35 kg/cm$^2$). The vapor stream is initially cooled in the dephlegmator to 168° K. and split into a portion (line 42) going to hydrogen recovery and a high pressure stream (line 43). The high pressure stream is flashed via J-T valve 44 to a reduced pressure of 370 psia (26 kg/cm$^2$) with resulting reduction in temperature to 161° K. and is passed through the dephlegmator as a refrigerant via line 46. The exiting stream in line 48 at 173° K. is further reduced in pressure by work expansion in turbine 50 to a pressure of 123 psia (8.65 kg/cm$^2$) with resulting reduction in temperature to 139° K. and is returned as refrigerant in the dephlegmator via line 51.

The several streams recovered from the dephlegmator have the following compositions respectively

|  | Mols | | |
| --- | --- | --- | --- |
| Stream | 25 | 45 | 52 |
| Hydrogen | 6.18 | 22.5 | 262.8 |
| Carbon Monoxide | 0.15 | 0.09 | 1.08 |
| Methane | 293.9 | 60.18 | 703.0 |
| Acetylene | 0.05 | .002 | 0.02 |
| Ethylene | 19.68 | 0.132 | 1.55 |
| Ethane | 0.68 | .0006 | .007 |
| Total | 320.6 | 82.9 | 968.5 |

The off gases discharged from the dephlegmator through lines 45 and 52 contain less than 0.2 mol % ethylene, which constitutes about 0.3% of that initially charged to the demethanizer column.

The liquid bottoms fraction recovered from the demethanizer column (line 35, FIG. 1) at 505 psia (35.5 kg/cm$^2$) and 289° K. comprises:

|  | Mols |
| --- | --- |
| Methane | 0.04 |
| Acetylene | 3.88 |
| Ethylene | 566.8 |
| Ethane | 154.3 |
| $C_3+$ | 285.0 |
| Total | 1010.0 |

The ethylene recovery from the dephlegmator constitutes 92+% of that present in the vapor feed charged to the dephlegmator, in addition to which 99% or more of the ethane is recovered.

The previous examples are preferably employed where low H$_2$ recovery is acceptable, since, as in Example 1 (FIG. 1), C$_2$ hydrocarbons are not recovered from the stream (line 20) sent to the H$_2$ recovery unit. In Example 2 (FIG. 2), C$_2$ hydrocarbons are recovered from the stream (line 45) sent to H$_2$ recovery, however, since the stream does not undergo pressure reduction, no refrigeration is obtained from the stream and some C$_2$ hydrocarbon recovery is therefore lost.

It will be understood that the foregoing examples are for purposes of illustrating operations in accordance with the invention and the operating conditions therein disclosed are subject to variation without departing from the essential features of the invention as defined in the appended claims.

What is claimed:

1. The method of obtaining enhanced recovery of C$_2$ hydrocarbons from the vapor overhead of a demethanizer column charged with a composition containing C$_2$ hydrocarbons in admixture with hydrogen, methane and C$_3+$ hydrocarbons, which comprises the steps of condensing a portion of said overhead vapors, returning the condensate as main reflux to the demethanizer column, introducing the uncondensed vapors as a stream containing residual C$_2$ hydrocarbons into a dephlegmation zone for upward flow therein in indirect heat exchange with refrigerant supplied to passages in said dephlegmator, thereby effecting condensation on the walls of said passages of components of said stream including said C$_2$ hydrocarbons, said condensed components forming a reflux liquid such that interaction takes place between the upwardly flowing vapors and the downwardly flowing liquid such that the liquid becomes enriched in C$_2$ hydrocarbons, withdrawing the thus formed downwardly flowing liquid for recovery of the C$_2$ hydrocarbons contained therein in the liquid bottoms withdrawn from said demethanizer column, reducing the pressure of an uncondensed portion of said upwardly flowing vapors, and introducing the cold fluid stream from the pressure reduction of said uncondensed portion into the passages in said dephlegmation zone to serve as the only refrigerant supplied to said passages.

2. The method as defined in claim 1 wherein the C$_2$ hydrocarbon enriched liquid stream withdrawn from said dephlegmation zone is returned directly to said demethanizer column as auxiliary reflux for recovery of the C$_2$ hydrocarbons contained therein in the liquid bottoms withdrawn from said demethanizer column.

3. The method as defined in claim 1 wherein said pressure reduction of said upwardly flowing vapors is effected by passage through a Joule-Thompson expansion valve.

4. The method as defined in claim 1 wherein said pressure reduction of said upwardly flowing vapors is effected by work expansion.

5. The method as defined in claim 4 wherein the vapor stream first introduced into said dephlegmation zone comprises up to about 2% ethylene, more than 85% of which ethylene is recovered in the $C_2$ enriched liquid stream returned to said demethanizer column.

6. The method as defined in claim 3 wherein the vapor stream first introduced into said dephlegmation zone comprises up to about 2% ethylene, more than 60% of which ethylene is recovered in the $C_2$ enriched liquid stream returned to said demethanizer column.

7. The method as defined in claim 1 wherein said uncondensed vapor stream is initially introduced into said dephlegmation zone at a pressure of 28 to 42 kg/cm² absolute and at a temperature of 170° to 195° K.

8. The method as defined in claim 7 wherein said $C_2$ enriched liquid stream is withdrawn from said dephlegmation zone at a temperature in the range of 168° to 194° K.

9. The method as defined in claim 1 wherein said upwardly flowing vapors from said dephlegmation zone are further partially condensed and separated into a $H_2$ enriched vapor stream and a $C_1$ enriched liquid stream prior to pressure reduction of at least one of said streams for refrigeration supply to the dephlegmation zone.

10. The method as defined in claim 9 wherein said upwardly flowing vapors from said dephlegmation zone are partially condensed in a heat exchanger zone and the resulting partially condensed vapor stream is separated into the $H_2$ enriched vapor stream and the $C_1$ enriched liquid stream.

* * * * *